United States Patent
Grubb

(10) Patent No.: US 7,297,688 B2
(45) Date of Patent: Nov. 20, 2007

(54) STARTER KIT FOR LOW DOSE ORAL CONTRACEPTIVES

(75) Inventor: Gary S. Grubb, Newtown Square, PA (US)

(73) Assignee: Wyeth, Madison, NJ (US)

( * ) Notice: Subject to any disclaimer, the term of this patent is extended or adjusted under 35 U.S.C. 154(b) by 502 days.

(21) Appl. No.: 09/872,250

(22) Filed: Jun. 1, 2001

(65) Prior Publication Data

US 2002/0010167 A1    Jan. 24, 2002

Related U.S. Application Data

(60) Provisional application No. 60/210,310, filed on Jun. 8, 2000.

(51) Int. Cl.
*A61K 33/56* (2006.01)
(52) U.S. Cl. ........................ 514/171; 514/182
(58) Field of Classification Search ............... 514/170, 514/178, 172, 182
See application file for complete search history.

(56) References Cited

U.S. PATENT DOCUMENTS

| 4,530,839 | A |   | 7/1985 | Pasquale |
| 5,418,228 | A |   | 5/1995 | Bennink |
| 5,552,394 | A | * | 9/1996 | Hodgen ...................... 514/178 |
| 5,898,032 | A |   | 4/1999 | Hodgen |
| 6,027,749 | A |   | 2/2000 | Schmidt-Gollwitzer et al. |
| 6,133,251 | A |   | 10/2000 | Dittgen et al. |

FOREIGN PATENT DOCUMENTS

| WO | WO 97 41870 | 11/1997 |
| WO | WO 98 04268 | 2/1998 |
| WO | WO 99/12531 | 3/1999 |
| WO | WO 99/53910 | 10/1999 |

OTHER PUBLICATIONS

Nordette® monograph, Physicians' Desk Reference, 50th edition, 1996, p. 2755-2758.*
Alesse® monograph, electronic Physicians' Desk Reference, Apr. 1997.*
Katzung Basic & Clinical Pharmacology, 6th edition, 1995, p. 620.*
Endrikat et al., Contraception, 1997;55(3): 131-137.*
Goodman and Gilman's the Pharmacological Basis of Therapeutics, 9th ed., p. 1420-1421.*
J. Endrikat et al., Contraception, 1997, 131-137, 55.
M. Akerlund et al., Br. J. Obstetrics and Gynaecology, 1993, 832-8, 100(9).

* cited by examiner

*Primary Examiner*—San-ming Hui
(74) *Attorney, Agent, or Firm*—Arnold S. Milowsky; Michael A. Patané; Pepper Hamilton LLP

(57) ABSTRACT

The present invention provides a contraceptive kit which helps to overcome or ameliorate the problem of breakthrough bleeding and spotting associated with lowest dose (15-20 ug EE) estrogen contraceptives.

11 Claims, No Drawings

STARTER KIT FOR LOW DOSE ORAL CONTRACEPTIVES

This application claims the benefit of U.S. Provisional Application No. 60/210,310, filed Jun. 8, 2000.

BACKGROUND OF THE INVENTION

Since the introduction of oral contraceptives (OCs) over a quarter-century ago, research has been directed toward developing preparations that minimize the potential for side effects while maintaining efficacy and normal menstrual patterns.

During the first three to four months oral contraceptive use, the incidence rate of breakthrough bleeding and spotting rates in the first cycle are about two times higher than the rate that remains generally steady after cycle 4. This is due to the change in endometrial histology over several months of OC use that is due to a progestin effect from an OC. Several months of OC use produces a more secretory endometrium which is less prone to breakthrough bleeding. Breakthrough bleeding and spotting are the most common complaint by women first using OCs and is a common reason for discontinuing use of OCs. Breakthrough bleeding and spotting rates are higher with OCs containing amounts of estrogen less than about 30 ug, particularly in the first several months of use.

Using a constant dose of progestin, Endrikat et al., 1997 found that the break through bleeding/spotting rate for 30 ug ethinyl estradiol (EE) OC as compared to 20 ug EE OC was 68% in cycle 1, 85% in cycle 2 and 67% in cycle 3. Similarly, Akerlund et al. (1993) found that the BTB/S rate for 30 ug EE OC as compared to 20 ug EE OC was 77% in cycle 1, 60% in cycle 2 and 67% in cycle 3. These results are consistent with the conversion to a secretory endometrium occuring more quickly with an OC containing higher EE doses.

The present invention provides a contraceptive kit which helps to overcome or ameliorate the problem of breakthrough bleeding and spotting associated with lowest dose (15-20 ug EE) estrogen contraceptives.

DETAILED DESCRIPTION OF THE INVENTION

In accordance with the present invention is provided an oral contraceptive starter kit comprising two or more cycle packs of oral contraceptives containing an estrogen and a progestin, and having a first and a last cycle pack, the effective dosage of steroid in the first cycle pack being greater than in subsequent cycle packs, the last cycle pack providing the smallest amount of effective steroid dosage, and no more than about 20 ug EE per dosage unit. The starter kit provides a means to gradually decrease the dose of estrogen over a number of cycles, thereby decreasing incidences of breakthrough bleeding and spotting that are often associated the lose-dose estrogen contraceptives. Thus, a first cycle may contain, for example, 30 ug of estrogen per dosage unit. A second cycle may contain 30 ug of estrogen per dosage unit. A third cycle may contain 20 ug of estrogen per dosage unit. Following the completion of the starter kit, standard cycle packs of lowest dose EE OC may be used.

Cycle pack, as used herein, refers to an oral contraceptive pill pack generally containing from 21-25 consecutive days of active ingredient-containing dosage units and may also contain placebos for the remainder of the cycle (3 to 7 days), which are free of hormonal active ingredient. Dosage units in the form of tablets or capsules may also contain excipients such as binders, diluents, disintegrating agents and lubricating agents. Placebos of the cycle pack may contain non-hormonal active agents such as iron or folic acid.

Effective dose refers to the combined amount of steroid in a daily dosage unit taking into account the potency of a given steroid. The effective dose of a given steroid can be determined by one skilled in the art.

Hormonal active ingredients useful as oral contraceptives are well known in the art. Generally oral contraceptives contain an estrogen and a progestin. Hormonal active ingredients may be formulated as monophasic, biphasic or triphasic.

Suitable estrogens include 17-β estradiol, estrone, or a salt thereof, estriol, ethinylestradiol and mestranol.

Suitable progestins include trimegestone, nomegestrol, dienogest, norgestrel, levonorgestrel, cyproterone acetate, 3-ketodesogestrel (or etonogestrel), desogestrel, gestodene, norethindrone, drospirenone, medroxy progesterone acetate, megestrol acetate, norgestimate, 17B deactyl norgestimate, osaterone, norethindrone acetate, lynestrenol, norethynodrel, and ethynodiol diacetate. Combination oral contraceptives (containing estrogen and progestins) are commercially available such as those sold under the tradenames Alesse®, Brevicon®, Demulen®, Desogen®, Estrostep®, Harmonet®, Levlen®, Levlite®, Levora®, Loestrin®, Loette®, LoOvral®, Micronor®, Minesse®, Minulet®, Mircette®, Modicon®, Necon®, Nordette®, Norinyl®, Ortho-cept®, Ortho-Cyclen®, Ortho-Novum®, Ortho-Tri-Cyclen®, Ovcon®, Ovral®, Ovrette®, Trilevlen®, Trimiron®, TriMinulet®, Tri-Norinyl®, Triphasil®, Trivora®, and Zovia®.

Kits of the present invention may contain multiple cycles dosages of various combination oral contraceptive arranged to appropriately decrease the effective dosage of total steroid from the penultimate cycle pack to the last cycle pack. For instance, a kit of the present invention might combine as a first cycle Nordette®, as a second cycle Triphasil® and as a third cycle Alesse®. Alternatively, a kit of the present invention might combined first and second cycles of Nordette®, third and fourth cycles of Triphasil® and a fifth cycle of Alesse®. In another embodiment of the invention, the kit might present a first cycle of Levora®, a second cycle of Trilevora® or Trilevlen® and a third cycle of Levlite®. In yet another embodiment of the invention, a first cycle of Loestrin® 1.5/30, a second cycle of Estrostep® and a third cycle of Loestrin® 1/20 might be combined. Similarly, a first cycle of Ortho-Novum® 1/35, a second cycle of Ortho-Novum® 7/7/7 and a third cycle of an OC containing norethindrone and an EE dose of less than or equal to 30 ug are combined in a starter kit. More detailed examples of cycles and dosages are described in the Examples.

Although not required, in some preferred embodiments of the present invention the progestin and estrogen should be the same, although the dosages are varied throughout the cycles of the kit.

Each cycle may range in duration from 21-25 consecutive days of steroid, followed by non-contraceptive placebos for the remainder of each cycle (i.e. 3-7 days). The kit may contain daily dosages arranged in dispensers such as blister packs or dial pack dispensers.

The starter kit may contain 2 or more single cycle dosage arrangements, or the cycles may be combined to form a multi-cycle dosage arrangement. The starter kit may also contain instructional materials, markings or arrangements which explain the use and order of the cycle packs.

In multi-cycle dosage arrangements the cycles may be separated from one another spatially and/or by other markings. Alternatively, blister packs containing individual cycles may be separated by perforations in the base of the blister pack or other means suitable for separation.

EXAMPLES

The following examples are illustrative but are not meant to be limiting of the present invention. Each examples describes regimens of combination oral contraceptives which can be used to decrease the incidence of break through bleeding and spotting associated with the lowest dose (15-20 ug) estrogen contraceptives.

EXAMPLE 1

| Compound | Amount (dosage unit) | Duration | Cycle |
|---|---|---|---|
| LNG (levonorgestrel) | 150 ug | 21 days | 1 |
| EE (ethinyl estradiol) | 30 ug | | |
| LNG | 50 ug | 6 days | 2 |
| EE | 30 ug | | |
| LNG | 75 ug | 5 days | |
| EE | 40 ug | | |
| LNG | 125 mg | 10 days | |
| EE | 30 ug | | |
| LNG | 100 ug | 21 days | 3 |
| EE | 20 ug | | |

EXAMPLE 2

| Compound | Amount (dosage unit) | Duration | Cycle |
|---|---|---|---|
| LNG (levonorgestrel) | 150 ug | 21 days | 1, 2 |
| EE (ethinyl estradiol) | 30 ug | | |
| LNG | 50 ug | 6 days | 3, 4 |
| EE | 30 ug | | |
| LNG | 75 ug | 5 days | |
| EE | 40 ug | | |
| LNG | 125 mg | 10 days | |
| EE | 30 ug | | |
| LNG | 100 ug | 21 days | 5 |
| EE | 20 ug | | |

EXAMPLE 3

| Compound | Amount | Duration | Cycle |
|---|---|---|---|
| NETA (norethindrone acetate) | 1.5 mg | 21 days | 1 |
| EE | 30 ug | | |
| NETA | 1 mg | 5 days | 2 |
| EE | 20 ug | | |
| NETA | 1 mg | 7 days | |
| EE | 30 ug | | |
| NETA | 1 mg | 9 days | |
| EE | 35 ug | | |
| NETA | 1 mg | 21 days | 3 |
| EE | 20 ug | | |

EXAMPLE 4

| Compound | Amount | Duration | Cycle |
|---|---|---|---|
| NET (norethindrone) | 1.0 mg | 21 days | 1 |
| EE | 35 ug | | |
| NET | 0.5 mg | 7 days | 2 |
| EE | 35 ug | | |
| NET | 0.75 mg | 7 days | |
| EE | 35 ug | | |
| NET | 1 mg | 7 days | |
| EE | 35 ug | | |
| NET | 1 mg | 21 days | 3 |
| EE | 25 ug | | |

EXAMPLE 5

| Compound | Amount | Duration | Cycle |
|---|---|---|---|
| GSD (gestodene) | 75 ug | 21 days | 1 |
| EE | 30 ug | | |
| GSD | 50 ug | 6 days | 2 |
| EE | 30 ug | | |
| GSD | 70 ug | 5 days | |
| EE | 40 ug | | |
| GSD | 100 ug | 10 days | |
| EE | 30 ug | | |
| GSD | 75 ug | 21 days | 3 |
| EE | 20 ug | | |

EXAMPLE 6

| Compound | Amount | Duration | Cycle |
|---|---|---|---|
| GSD | 50 ug | 6 days | 1 |
| EE | 30 ug | | |
| GSD | 70 ug | 5 days | |
| EE | 40 ug | | |
| GSD | 100 ug | 10 days | |
| EE | 30 ug | | |
| GSD | 75 ug | 21 days | 2 |
| EE | 30 ug | | |
| GSD | 75 ug | 24 days | 3 |
| EE | 20 ug | | |

EXAMPLE 7

| Compound | Amount | Duration | Cycle |
|---|---|---|---|
| GSD | 75 ug | 21 days | 1 |
| EE | 30 ug | | |
| GSD | 75 ug | 21 days | 2 |
| EE | 20 ug | | |
| GSD | 60 ug | 24 days | 3 |
| EE | 15 ug | | |

EXAMPLE 8

| Compound | Amount | Duration | Cycle |
|---|---|---|---|
| GSD | 75 ug | 21 days | 1, 2 |
| EE | 30 ug | | |
| GSD | 75 ug | 21 days | 3, 4 |
| EE | 20 ug | | |
| GSD | 60 ug | 24 days | 5 |
| EE | 15 ug | | |

EXAMPLE 9

| Compound | Amount | Duration | Cycle |
|---|---|---|---|
| GSD | 75 ug | 21 days | 1 |
| EE | 30 ug | | |
| GSD | 50 ug | 6 days | 2 |
| EE | 30 ug | | |

EXAMPLE 9-continued

| Compound | Amount | Duration | Cycle |
|---|---|---|---|
| GSD | 70 ug | 5 days | |
| EE | 40 ug | | |
| GSD | 100 ug | 10 days | |
| EE | 30 ug | | |
| GSD | 60 ug | 24 days | 3 |
| EE | 15 ug | | |

EXAMPLE 10

| Compound | Amount | Duration | Cycle |
|---|---|---|---|
| DSG | 250 ug | 21 days | 1 |
| EE | 30 ug | | |
| DSG | 50 ug | 7 days | 2 |
| EE | 35 ug | | |
| DSG | 100 ug | 7 days | |
| EE | 30 ug | | |
| DSG | 150 ug | 7 days | |
| EE | 30 ug | | |
| DSG | 150 ug | 21 days | 3 |
| EE | 20 ug | | |
| EE | 10 ug | 5 days | |

EXAMPLE 11

| Compound | Amount | Duration | Cycle |
|---|---|---|---|
| NGM | 250 ug | 21 days | 1 |
| EE | 30 ug | | |
| NGM | 180 ug | 7 days | 2 |
| EE | 35 ug | | |
| NGM | 215 ug | 7 days | |
| EE | 35 ug | | |
| NGM | 250 ug | 7 days | |
| EE | 30 ug | | |
| NGM | 250 ug | 21 days | 3 |
| EE | 20 ug | | |

EXAMPLE 12

| Compound | Amount | Duration | Cycle |
|---|---|---|---|
| NGM (norgestimate) | 250 ug | 21 days | 1, 2 |
| EE | 30 ug | | |
| NGM | 180 ug | 7 days | 3, 4 |
| EE | 35 ug | | |

EXAMPLE 12-continued

| Compound | Amount | Duration | Cycle |
|---|---|---|---|
| NGM | 215 ug | 7 days | |
| EE | 35 ug | | |
| NGM | 250 ug | 7 days | |
| EE | 30 ug | | |
| NGM | 250 ug | 21 days | 5 |
| EE | 20 ug | | |

What is claimed is:

1. An oral contraceptive starter kit comprising at least two cycle packs of oral contraceptives containing an estrogen and a progestin, and having a penultimate and a last cycle pack, the effective dosage of steroid in the penultimate cycle pack being greater than the effective dosage of steroid in the last cycle pack, the last cycle pack providing no more than about 20 ug estrogen per dosage unit.

2. The starter kit of claim 1 wherein the cycle packs are packaged in individual units.

3. The starter kit of claim 1 wherein multiple cycle packs are packaged together as a single unit.

4. The starter kit of claim 1 further comprising written instructions describing the order of use of said cycle packs.

5. The starter kit of claim 1 wherein the estrogen is ethinylestradiol.

6. The starter kit of claim 1 wherein the progestin is selected from the group consisting of trimegestone, nomegestrol, norgestrel, levonorgestrol, cyproterone acetate, 3-ketodesogestrel, desogestrel, gestodene, drospirenone, medroxy progesterone acetate, megestrol acetate, norgestimate, 17B deactyl norgestimate, osaterone, norethindrone, norethindrone acetate, lynestrenol, norethynodrel, and ethynodiol diacetate.

7. The starter kit of claim 1 wherein the estrogen is ethinylestradiol and the progestin is levonorgestrel.

8. The starter kit of claim 1 wherein the estrogen is ethinylestradiol and the progestin is norethindrone.

9. The starter kit of claim 1 wherein the estrogen is ethinylestradiol and the progestin is norethindrone acetate.

10. The starter kit of claim 1 wherein the estrogen is ethinylestradiol and the progestin is gestodene.

11. The starter kit of claim 1 wherein the estrogen is ethinylestradiol and the progestin is norgestimate.

* * * * *

UNITED STATES PATENT AND TRADEMARK OFFICE
CERTIFICATE OF CORRECTION

PATENT NO. : 7,297,688 B2
APPLICATION NO. : 09/872250
DATED : November 20, 2007
INVENTOR(S) : Gary S. Grubb It is certified that error appears in the above-identified patent and that said Letters Patent is hereby corrected as shown below:

In column 2, please correct the paragraph spanning lines 14-15 as follows:

Suitable estrogens include 17β-estradiol, estrone, or a salt thereof, estriol, ~~ethinylestradiol~~ ethinyl estradiol and mestranol.

In column 3, please correct the Tables labeled Example 1 and Example 2 as follows:

EXAMPLE 1

| Compound | Amount (dosage unit) | Duration | Cycle |
|---|---|---|---|
| LNG (levonorgestrel) | 150 ug | 21 days | 1 |
| EE (ethinyl estradiol) | 30 ug | | |
| LNG | 50 ug | 6 days | 2 |
| EE | 30 ug | | |
| LNG | 75 ug | 5 days | |
| EE | 40 ug | | |
| LNG | 125 ~~mg~~ ug | 10 days | |
| EE | 30 ug | | |
| LNG | 100 ug | 21 days | 3 |
| EE | 20 ug | | |

EXAMPLE 2

| Compound | Amount (dosage unit) | Duration | Cycle |
|---|---|---|---|
| LNG (levonorgestrel) | 150 ug | 21 days | 1, 2 |
| EE (ethinyl estradiol) | 30 ug | | |
| LNG | 50 ug | 6 days | 3, 4 |
| EE | 30 ug | | |
| LNG | 75 ug | 5 days | |
| EE | 40 ug | | |
| LNG | 125 ~~mg~~ ug | 10 days | |
| EE | 30 ug | | |
| LNG | 100 ug | 21 days | 5 |
| EE | 20 ug | | |

UNITED STATES PATENT AND TRADEMARK OFFICE
CERTIFICATE OF CORRECTION

PATENT NO. : 7,297,688 B2
APPLICATION NO. : 09/872250
DATED : November 20, 2007
INVENTOR(S) : Gary S. Grubb It is certified that error appears in the above-identified patent and that said Letters Patent is hereby corrected as shown below:

In column 5, please correct the tables labeled Example 10 and Example 11 as follows:

EXAMPLE 10

| Compound | Amount (dosage unit) | Duration | Cycle |
|---|---|---|---|
| DSG (desogestrol) | 250 ug | 21 days | 1 |
| EE | 30 ug | | |
| DSG | 50 ug | 7 days | 2 |
| EE | 35 ug | | |
| DSG | 100 ug | 7 days | |
| EE | 30 ug | | |
| DSG | 150 ug | 7 days | |
| EE | 30 ug | | |
| DSG | 150 ug | 21 days | 3 |
| EE | 20 ug | | |
| EE | 10 ug | 5 days | |

EXAMPLE 11

| Compound | Amount (dosage unit) | Duration | Cycle |
|---|---|---|---|
| NGM (norgestimate) | 250 ug | 21 days | 1 |
| EE | 30 ug | | |
| NGM | 180 | 7 days | 2 |
| EE | 35 ug | | |
| NGM | 215 ug | 7 days | |
| EE | 35 ug | | |
| NGM | 250 ug | 7 days | |
| EE | 30 ug | | |
| NGM | 250 ug | 21 days | 3 |
| EE | 20 ug | | |

In claim 3, please amend the claim as follows:

3. The starter kit of claim 1 wherein ~~miltiple~~ <u>multiple</u> cycle packs are packaged together as a single unit.

UNITED STATES PATENT AND TRADEMARK OFFICE
CERTIFICATE OF CORRECTION

PATENT NO. : 7,297,688 B2
APPLICATION NO. : 09/872250
DATED : November 20, 2007
INVENTOR(S) : Gary S. Grubb It is certified that error appears in the above-identified patent and that said Letters Patent is hereby corrected as shown below:

In claim 5, please amend the claims as follows:

5. The starter kit of claim 1 wherein the estrogen is ~~ethinylestradiol~~ <u>ethinyl estradiol.</u>

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,297,688 B2  Page 1 of 3
APPLICATION NO. : 09/872250
DATED : November 20, 2007
INVENTOR(S) : Gary S. Grubb It is certified that error appears in the above-identified patent and that said Letters Patent is hereby corrected as shown below:

In column 2, please correct the paragraph spanning lines 14-15 as follows:

Suitable estrogens include 17β-estradiol, estrone, or a salt thereof, estriol, ~~ethinylestradiol~~ ethinyl estradiol and mestranol.

In column 3, please correct the Tables labeled Example 1 and Example 2 as follows:

EXAMPLE 1

| Compound | Amount (dosage unit) | Duration | Cycle |
|---|---|---|---|
| LNG (levonorgestrel) | 150 ug | 21 days | 1 |
| EE (ethinyl estradiol) | 30 ug | | |
| LNG | 50 ug | 6 days | 2 |
| EE | 30 ug | | |
| LNG | 75 ug | 5 days | |
| EE | 40 ug | | |
| LNG | 125 ~~mg~~ ug | 10 days | |
| EE | 30 ug | | |
| LNG | 100 ug | 21 days | 3 |
| EE | 20 ug | | |

EXAMPLE 2

| Compound | Amount (dosage unit) | Duration | Cycle |
|---|---|---|---|
| LNG (levonorgestrel) | 150 ug | 21 days | 1, 2 |
| EE (ethinyl estradiol) | 30 ug | | |
| LNG | 50 ug | 6 days | 3, 4 |
| EE | 30 ug | | |
| LNG | 75 ug | 5 days | |
| EE | 40 ug | | |
| LNG | 125 ~~mg~~ ug | 10 days | |
| EE | 30 ug | | |
| LNG | 100 ug | 21 days | 5 |
| EE | 20 ug | | |

UNITED STATES PATENT AND TRADEMARK OFFICE
CERTIFICATE OF CORRECTION

PATENT NO. : 7,297,688 B2
APPLICATION NO. : 09/872250
DATED : November 20, 2007
INVENTOR(S) : Gary S. Grubb It is certified that error appears in the above-identified patent and that said Letters Patent is hereby corrected as shown below:

In column 5, please correct the tables labeled Example 10 and Example 11 as follows:

EXAMPLE 10

| Compound | Amount (dosage unit) | Duration | Cycle |
|---|---|---|---|
| DSG (desogestrol) | 250 ug | 21 days | 1 |
| EE | 30 ug | | |
| DSG | 50 ug | 7 days | 2 |
| EE | 35 ug | | |
| DSG | 100 ug | 7 days | |
| EE | 30 ug | | |
| DSG | 150 ug | 7 days | |
| EE | 30 ug | | |
| DSG | 150 ug | 21 days | 3 |
| EE | 20 ug | | |
| EE | 10 ug | 5 days | |

EXAMPLE 11

| Compound | Amount (dosage unit) | Duration | Cycle |
|---|---|---|---|
| NGM (norgestimate) | 250 ug | 21 days | 1 |
| EE | 30 ug | | |
| NGM | 180 | 7 days | 2 |
| EE | 35 ug | | |
| NGM | 215 ug | 7 days | |
| EE | 35 ug | | |
| NGM | 250 ug | 7 days | |
| EE | 30 ug | | |
| NGM | 250 ug | 21 days | 3 |
| EE | 20 ug | | |

Column 6, lines 22 and 23

In claim 3, please amend the claim as follows:

3. The starter kit of claim 1 wherein ~~miltiple~~ <u>multiple</u> cycle packs are packaged together as a single unit.

UNITED STATES PATENT AND TRADEMARK OFFICE
CERTIFICATE OF CORRECTION

PATENT NO. : 7,297,688 B2
APPLICATION NO. : 09/872250
DATED : November 20, 2007
INVENTOR(S) : Gary S. Grubb It is certified that error appears in the above-identified patent and that said Letters Patent is hereby corrected as shown below:

Column 6, lines 26 and 27

In claim 5, please amend the claims as follows:

5. The starter kit of claim 1 wherein the estrogen is ~~ethinylestradiol~~ <u>ethinyl estradiol.</u>

This certificate supersedes the Certificate of Correction issued June 17, 2008.

Signed and Sealed this

Twenty-second Day of July, 2008

JON W. DUDAS
*Director of the United States Patent and Trademark Office*